(12) United States Patent  (10) Patent No.: US 10,923,768 B2
Yu et al.  (45) Date of Patent: Feb. 16, 2021

(54) ALKYNYL-CONTAINING COMPOUND ADDITIVE FOR NON-AQUEOUS ELECTROLYTE SOLUTION, AND NON-AQUEOUS ELECTROLYTE SOLUTION FOR LITHIUM SECONDARY BATTERY AND LITHIUM SECONDARY BATTERY WHICH INCLUDE THE SAME

(71) Applicant: LG Chem, Ltd., Seoul (KR)

(72) Inventors: Sung Hoon Yu, Daejeon (KR); Kyung Mi Lee, Daejeon (KR); Shul Kee Kim, Daejeon (KR); Hyun Yeong Lee, Daejeon (KR); Yoo Sun Kang, Daejeon (KR)

(73) Assignee: LG Chem, Ltd.

( * ) Notice: Subject to any disclaimer, the term of this patent is extended or adjusted under 35 U.S.C. 154(b) by 0 days.

(21) Appl. No.: 16/086,451

(22) PCT Filed: Jan. 15, 2018

(86) PCT No.: PCT/KR2018/000700
§ 371 (c)(1),
(2) Date: Sep. 19, 2018

(87) PCT Pub. No.: WO2018/135822
PCT Pub. Date: Jul. 26, 2018

(65) Prior Publication Data
US 2019/0334207 A1   Oct. 31, 2019

(30) Foreign Application Priority Data

Jan. 23, 2017 (KR) .................. 10-2017-0010223

(51) Int. Cl.
*H01M 10/0567*   (2010.01)
*C07C 43/315*    (2006.01)
(Continued)

(52) U.S. Cl.
CPC ....... *H01M 10/0567* (2013.01); *C07C 43/315* (2013.01); *C07C 57/18* (2013.01);
(Continued)

(58) Field of Classification Search
CPC ......... H01M 10/0567; H01M 10/0568; H01M 10/0569; C07C 43/315; C07C 57/18; C07D 303/22
(Continued)

(56) References Cited

U.S. PATENT DOCUMENTS 2,986,569 A * 5/1961 Monroe ............... C07D 303/22
549/555
7,033,707 B2   4/2006 Gan et al.
(Continued)

FOREIGN PATENT DOCUMENTS

CN   100502135 C   6/2009
CN   103380530 A   10/2013
(Continued)

OTHER PUBLICATIONS

Saravanan et al. Click Chemistry-Assisted Triazole-Substituted Azobenzene and Fulgimide Units in the Pendant-Based Copoly(decyloxymethacryate)s for Dual-Mode Optical Swiches, 2008, Journal of Polymer Science: Part A: Polymer Chemistry, 46, 7843-7860 (Year: 2008).*

(Continued)

*Primary Examiner* — Sean P Cullen
(74) *Attorney, Agent, or Firm* — Lerner, David, Littenberg, Krumholz & Mentlik, LLP (57) ABSTRACT

The present invention relates to an additive for a non-aqueous electrolyte solution, which may suppress the generation of metallic foreign matter causing a side effect in a battery while forming a stable film on the surface of an electrode, a non-aqueous electrolyte solution for a lithium
(Continued)

secondary battery which includes the additive, and a lithium secondary battery including the non-aqueous electrolyte solution.

8 Claims, 1 Drawing Sheet

(51) Int. Cl.
  *C07C 57/18* (2006.01)
  *C07D 303/22* (2006.01)
  *H01M 10/0525* (2010.01)
  *H01M 10/0568* (2010.01)
  *H01M 10/0569* (2010.01)

(52) U.S. Cl.
  CPC ...... *C07D 303/22* (2013.01); *H01M 10/0525* (2013.01); *H01M 10/0568* (2013.01); *H01M 10/0569* (2013.01); *H01M 2300/0037* (2013.01)

(58) Field of Classification Search
  USPC .......................................................... 429/332
  See application file for complete search history.

(56) References Cited

U.S. PATENT DOCUMENTS

| | | | |
|---|---|---|---|
| 2006/0177742 | A1 | 8/2006 | Abe et al. |
| 2008/0038644 | A1 | 2/2008 | Abe et al. |
| 2010/0092872 | A1 | 4/2010 | Abe et al. |
| 2011/0045361 | A1 | 2/2011 | Abe et al. |
| 2011/0281177 | A1 | 11/2011 | Xu |
| 2012/0301797 | A1 | 11/2012 | Abe et al. |
| 2013/0059210 | A1 | 3/2013 | Yu et al. |
| 2013/0309564 | A1 | 11/2013 | Yoshida et al. |
| 2013/0316229 | A1* | 11/2013 | Sawa ................ H01M 10/052 429/200 |
| 2013/0330609 | A1* | 12/2013 | Sawa ............... H01M 10/0525 429/200 |
| 2015/0037667 | A1 | 2/2015 | Suguro et al. |
| 2015/0140448 | A1* | 5/2015 | Takiguchi ........ H01M 10/0569 429/332 |
| 2015/0333280 | A1 | 11/2015 | Stoessel et al. |
| 2015/0364794 | A1* | 12/2015 | Nakazawa ....... H01M 10/0525 429/200 |
| 2016/0013517 | A1* | 1/2016 | Nakazawa ............ H01M 4/405 429/200 |
| 2016/0172708 | A1 | 6/2016 | Porta Garcia et al. |
| 2016/0322669 | A1* | 11/2016 | Sawa ............... H01M 10/0525 |
| 2017/0162906 | A1* | 6/2017 | Nakazawa ....... H01M 10/0569 |
| 2017/0200976 | A1* | 7/2017 | Nakazawa ............ H01M 4/587 |
| 2017/0301947 | A1 | 10/2017 | Makino et al. |
| 2018/0065908 | A1 | 3/2018 | Xia et al. |
| 2018/0076488 | A1 | 3/2018 | Shi et al. |

FOREIGN PATENT DOCUMENTS

| | | | |
|---|---|---|---|
| CN | 103608962 | A | 2/2014 |
| CN | 105428717 | A | 3/2016 |
| DE | 102007063051 | A1 | 7/2009 |
| EP | 1758198 | A1 | 2/2007 |
| EP | 2768064 | A1 | 8/2014 |
| JP | 3169248 | B2 | 5/2001 |
| JP | 2001256995 | A * | 9/2001 |
| JP | 2001256995 | A | 9/2001 |
| JP | 2002124297 | A | 4/2002 |
| JP | 2003059529 | A | 2/2003 |
| JP | 2005248165 | A | 9/2005 |
| JP | 2006213617 | A | 8/2006 |
| JP | 2007242496 | A * | 9/2007 |
| JP | 2008050281 | A | 3/2008 |
| JP | 2010050020 | A | 3/2010 |
| JP | 2010182688 | A | 8/2010 |
| JP | 2015099660 | A * | 5/2015 |
| JP | 2016531389 | A | 10/2016 |
| KR | 20070018966 | A | 2/2007 |
| KR | 20100031019 | A | 3/2010 |
| KR | 101158143 | B1 | 6/2012 |
| KR | 20120124424 | A | 11/2012 |
| KR | 20130026282 | A | 3/2013 |
| KR | 101533121 | B1 | 7/2015 |
| WO | WO-2011034828 | A1 * | 3/2011 .............. A61P 25/08 |
| WO | 2013115041 | A1 | 8/2013 |
| WO | 2013180923 | A1 | 12/2013 |
| WO | 2014094961 | A1 | 6/2014 |
| WO | 2015007659 | A1 | 1/2015 |
| WO | 2016129428 | A1 | 8/2016 |
| WO | 2016180297 | A1 | 11/2016 |

OTHER PUBLICATIONS

Grigg et al., Palladium catalysed synthesis of pyrroles from enamines, 2000, Chemical Communications, 10, 873-874 (Year: 2000).*
Jacobson et al., The Addition of Alcohols to Vinylacetylene, 1934, Journal of the American Chemical Society, 56, 1169-1170 (Year: 1934).*
Johnson et al., 1,1-Diethoxy-3-(triphenylstannyl)-2-propyne, 1957, The Journal of Organic Chemsitry, 23, 738-740 (Year: 1957).*
Henbest et al., 720. Researches on Acetylenic Compounds. Part XXVI. Further Remformatsky Reactions with Propargyl Bromides, 1950, 3646-3650 (Year: 1950).*
Golas et al., Catalyst Performance in "Click" Coupling Reactions of Polymers Prepared by ATRP: Ligand and Metal Effects, 2006, Macromolecules, 39, 6451-6457 (Year: 2006).*
International Search Report for Application No. PCT/KR2018/000700 dated Apr. 27, 2018.
Christopher J. Easton et al: "Electrochemical and yeast-catalysed ring-opening of isoxazoles in the synthesis of analogues of the herbicide Grasp", The Royal Chemical Society. Journal. Perkin Transactions 1, No. 10, Jan. 1, 2001, pp. 1168-1174, XP055573882.
Daniel T. Gryko et al: "Synthesis of "Porphyrin-Linker-Thiol" Molecules with Diverse Linkers for Studies of Molecular-Based Information Storage", Journal of Organic Chemistry, vol. 65, No. 22, Nov. 1, 2000, pp. 7345-7355, XP055573888.
Extended European Search Report for Application No. 18741985.8 dated Apr. 4, 2019, 13 pages.
Frank Koster et al: "Electrochemical Selective Incorporation of CO2 into Terminal Alkynes and Diynes", European Journal of Organic Chemistry, vol. 2001, No. 13, Jul. 1, 2001, pp. 2507-2511, XP055573892.
Kinji Yamada et al: "A Convenient and General Synthesis of 2-Alkynoates or 1-Alkynyl Aryl Ketones via the Reaction of Iodine with the Ate-complexes Obtained from Lithium Ethoxycarbonyl-or Aroylacetylenide and Trialkylboranes", Synthesis, vol. 1977, No. 10, Jan. 1, 1977, pp. 679-681, XP055573958.
Masao Tokuda et al: "C-Alkylation of ap-Acetylenic Esters using Electrochemically Generated Intermediates", Jan. 1, 1980, XP055573963, Retrieved from the Internet: <URL:https://pubs.rsc.org/en/content/articlepdf/1980/c3/c39800000188>, pp. 188-189.
Search Report from Chinese Office Action of Application No. 2018800015520 dated Nov. 2, 2020; 4 pages.

* cited by examiner

ALKYNYL-CONTAINING COMPOUND ADDITIVE FOR NON-AQUEOUS ELECTROLYTE SOLUTION, AND NON-AQUEOUS ELECTROLYTE SOLUTION FOR LITHIUM SECONDARY BATTERY AND LITHIUM SECONDARY BATTERY WHICH INCLUDE THE SAME

CROSS-REFERENCE TO RELATED APPLICATIONS

The present application is a national phase entry under 35 U.S.C. § 371 of International Application No. PCT/KR2018/000700 filed Jan. 15, 2018, which claims priority from Korean Patent Application No. 10-2017-0010223 filed Jan. 23, 2017, all of which are incorporated herein by reference.

TECHNICAL FIELD

The present invention relates to an additive for a non-aqueous electrolyte solution, and a non-aqueous electrolyte solution for a lithium secondary battery and a lithium secondary battery which include the same.

BACKGROUND ART

Recently, in line with miniaturization, lightweight, thin profile, and portable requirements in electronic devices according to the development of information and telecommunications industry, the need for high-energy and high-density batteries used as power sources of such electronic devices has increased.

A lithium battery, particularly, a lithium ion battery (LIB), as a battery that may best meet the need, has been adopted as power sources of many portable devices due to high energy density and ease of design. Recently, as the lithium ion battery is adapted as power sources for electric vehicles or power storage in addition to small electronic devices such as portable IT devices, there emerges research to allow the lithium ion battery to maintain excellent performance not only at room temperature but also in a more severe outside environment such as a high-temperature or low-temperature environment.

Lithium secondary batteries are mostly composed of a negative electrode and a positive electrode, which are capable of intercalating and deintercalating lithium ions, and a non-aqueous electrolyte solution in which an appropriate amount of a lithium salt, such as $LiPF_6$ and $LiBF_4$, is dissolved in a mixed carbonate-based organic solvent.

Since a positive electrode active material is structurally collapsed as charge and discharge of the lithium secondary battery proceed, metal ions are eluted from the surface of the positive electrode. The eluted metal ions are electrodeposited on the negative electrode to degrade the negative electrode. The degradation phenomenon tends to be more accelerated when the potential of the positive electrode is increased or the battery is exposed to high temperature.

In order to address this limitation, a method of adding compounds capable of forming a protective layer in the non-aqueous electrolyte solution, that is, a solid electrolyte interface (SEI) on the surface of the negative electrode has been suggested. However, another limitation may occur in which overall performance of the secondary battery is degraded as other side effects are caused by the compounds added to the electrolyte solution.

Thus, there is a continuous need to develop a non-aqueous electrolyte solution containing an additive which may improve performance and stability of the battery while minimizing the side effects.

Also, in a lithium secondary battery, a low-voltage phenomenon (voltage drop) occurs due to foreign matters included in raw materials or incorporated in a process, and since the phenomenon is intensified by a micro-short circuit in the battery, it is disadvantageous in that cell working stops. Since this disadvantage results in defects at the final stage of the manufacturing process, there is a significant loss.

PRIOR ART DOCUMENT

Japanese Patent Application Laid-open Publication No. 2001-256995
U.S. Pat. No. 7,033,707
Japanese Patent Application Laid-open Publication No. 2003-059529

DISCLOSURE OF THE INVENTION

Technical Problem

An aspect of the present invention provides an additive for a non-aqueous electrolyte solution which may suppress a side effect occurring due to metallic foreign matter in a battery while forming a stable film on the surface of an electrode.

Another aspect of the present invention provides a non-aqueous electrolyte solution for a lithium secondary battery which includes the additive for a non-aqueous electrolyte solution.

Another aspect of the present invention provides a lithium secondary battery which includes the non-aqueous electrolyte solution for a lithium secondary battery.

Technical Solution

According to an aspect of the present invention,
there is provided an additive for a non-aqueous electrolyte solution which comprises at least one compound selected from the group consisting of compounds represented by Formulae 1 and 2:

(Formula 1)

[Formula 2]

wherein, in Formula 1 or 2,
$R_1$ and $R_2$ are each independently hydrogen, an alkyl group having 1 to 6 carbon atoms, or alkoxy having 1 to 6 carbon atoms,
$R_3$ is an alkylene group having 1 to 3 carbon atoms,
$R_4$ and $R_6$ are each independently hydrogen, an alkyl group having 1 to 6 carbon atoms, an aryl group having 6 to 18 carbon atoms, a heterocycloalkyl group having 5 to 8 carbon atoms, an alkenyl group having 2 to 4 carbon atoms, or an alkynyl group having 2 to 4 carbon atoms, $R_5$ is an alkyl group having 1 to 6 carbon atoms or an alkyl group having 2 to 4 carbon atoms which includes an ether group, and n is an integer of 0 to 3.

In this case, in the compound represented by Formula 1, $R_1$ may be hydrogen or an alkyl group having 1 to 6 carbon atoms, $R_2$ may be hydrogen or alkoxy having 1 to 6 carbon atoms, $R_3$ may be an alkylene group having 1 to 3 carbon atoms, $R_4$ may be an alkyl group having 1 to 6 carbon atoms, an aryl group having 6 to 18 carbon atoms, a heterocycloalkyl group having 5 to 8 carbon atoms, or an alkynyl group having 2 to 4 carbon atoms, and n may be an integer of 0 to 3.

Specifically, the compound represented by Formula 1 may include at least one selected from the group consisting of compounds represented by Formulae 1a to 1g below.

(Formula 1a)
(Formula 1b)
(Formula 1c)
(Formula 1d)
(Formula 1e)
(Formula 1f)
(Formula 1g)

Also, in the compound represented by Formula 2, $R_5$ may be an alkyl group having 1 to 6 carbon atoms or an alkyl group having 2 to 4 carbon atoms which includes an ether group, and $R_6$ may be an alkyl group having 1 to 6 carbon atoms.

Specifically, the compound represented by Formula 2 may include at least one selected from the group consisting of compounds represented by Formulae 2a to 2f below.

(Formula 2a)
(Formula 2b)
(Formula 2c)

(Formula 2d)

(Formula 2e)

(Formula 2f)

According to another aspect of the present invention, there is provided a non-aqueous electrolyte solution for a lithium secondary battery including:

a lithium salt; an organic solvent; and the additive for a non-aqueous electrolyte solution of the present invention, wherein the additive includes at least one of the compounds represented by Formulae 1 and 2.

The additive for a non-aqueous electrolyte solution is included in an amount of 0.01 wt % to 10 wt %, for example, 0.5 wt % to 10 wt % based on a total weight of the non-aqueous electrolyte solution.

According to another aspect of the present invention, there is provided a lithium secondary battery including a negative electrode, a positive electrode, and a non-aqueous electrolyte solution, wherein the non-aqueous electrolyte solution is the non-aqueous electrolyte solution for a lithium secondary battery of the present invention.

Advantageous Effects

According to an embodiment of the present invention, since a compound including a propargyl group having metal ion adsorption performance is used as an additive for a non-aqueous electrolyte solution, a non-aqueous electrolyte solution, which may suppress the generation of metallic foreign matter capable of causing a side effect in a battery and may prevent a battery swelling phenomenon by forming a stable film on surfaces of a negative electrode and a positive electrode, may be prepared. Furthermore, a lithium secondary battery having improved cycle life characteristics at high temperature may be prepared by including the non-aqueous electrolyte solution.

BRIEF DESCRIPTION OF THE DRAWINGS

The following drawings attached to the specification illustrate preferred examples of the present invention by example, and serve to enable technical concepts of the present invention to be further understood together with detailed description of the invention given below, and therefore the present invention should not be interpreted only with matters in such drawings.

MODE FOR CARRYING OUT THE INVENTION

Hereinafter, the present invention will be described in more detail.

It will be understood that words or terms used in the specification and claims should be interpreted as having a meaning that is consistent with their meaning in the context of the relevant art and the technical idea of the invention, based on the principle that an inventor may properly define the meaning of the words or terms to best explain the invention.

In general, when overcharging of a secondary battery occurs, a structure of a positive electrode active material becomes in an unstable state while an excessive amount of lithium ions is discharged from a positive electrode. Accordingly, oxygen is released from the positive electrode active material, and the released oxygen causes a decomposition reaction of an electrolyte solution. Particularly, if the elution of metal ions from the positive electrode is increased under high-temperature conditions, the eluted metal ions are precipitated on a surface of a negative electrode, and thus, a low-voltage phenomenon occurs. The low-voltage phenomenon is also caused by metallic foreign matters which are included in raw materials of the lithium battery or incorporated in a process. That is, the foreign matters cause a micro-short circuit between the positive electrode and the negative electrode while the foreign matters are eluted during charge and precipitated on the surface of the negative electrode. A battery performance is degraded because the low-voltage phenomenon, in which a voltage of the battery is reduced, occurs due to the short circuit.

In the present invention, in order to improve these limitations, provided is a non-aqueous electrolyte solution including a compound, which contain a propargyl group having metal ion adsorption performance and is capable of forming a film on the surface of an electrode, as an additive, and thus, the generation of metallic foreign matter capable of causing a side effect in the battery may be suppressed.

Also, in the present invention, provided is a non-aqueous electrolyte solution for a lithium secondary battery which may improve overcharge safety of the electrolyte solution by including the non-aqueous electrolyte solution additive.

Furthermore, in the present invention, provided is a lithium secondary battery in which cycle characteristics and high-temperature storage performance are improved even during high-voltage charge by including the non-aqueous electrolyte solution.

Specifically, in an embodiment of the present invention, there is provided an additive for a non-aqueous electrolyte solution which comprises at least one compound selected from the group consisting of compounds represented by Formulae 1 and 2 below.

(Formula 1)

(Formula 2)

In Formula 1 or 2, $R_1$ and $R_2$ are each independently hydrogen, an alkyl group having 1 to 6 carbon atoms, or alkoxy having 1 to 6 carbon atoms, $R_3$ is an alkylene group having 1 to 3 carbon atoms, $R_4$ and $R_6$ are each independently hydrogen, an alkyl group having 1 to 6 carbon atoms, an aryl group having 6 to 18 carbon atoms, a heterocycloalkyl group having 5 to 8 carbon atoms, an alkenyl group having 2 to 4 carbon atoms, or an alkynyl group having 2 to 4 carbon atoms, $R_5$ is an alkyl group having 1 to 6 carbon atoms or an alkyl group having 2 to 4 carbon atoms which includes an ether group, and n is an integer of 0 to 3.

Specifically, in the compound represented by Formula 1, $R_1$ may be hydrogen or an alkyl group having 1 to 6 carbon atoms, $R_2$ may be hydrogen or alkoxy having 1 to 6 carbon atoms, $R_3$ may be an alkylene group having 1 to 3 carbon atoms, $R_4$ may be an alkyl group having 1 to 6 carbon atoms, an aryl group having 6 to 18 carbon atoms, a heterocycloalkyl group having 5 to 8 carbon atoms, or an alkynyl group having 2 to 4 carbon atoms, and n may be an integer of 0 to 3.

In this case, the aryl group may include any one selected from the group consisting of a phenyl group, a halophenyl group, a benzyl group, a halobenzyl group, a tolyl group, a naphthyl group, a trihalophenyl group, trihalomethylphenyl, halonitrobenzyl, an anthryl group, and a phenanthryl group.

Specifically, typical examples of the compound represented by Formula 1 may be at least one selected from the group consisting of compounds represented by Formulae 1a to 1g below.

(Formula 1a)

(Formula 1b)

(Formula 1c)

(Formula 1d)

(Formula 1e)

(Formula 1f)

(Formula 1g)

Also, in the compound represented by Formula 2, $R_5$ may be an alkyl group having 1 to 6 carbon atoms or an alkyl group having 2 to 4 carbon atoms which includes an ether group, and $R_6$ may be an alkyl group having 1 to 6 carbon atoms.

Specifically, typical examples of the compound represented by Formula 2 may be at least one selected from the group consisting of compounds represented by Formulae 2a to 2f below.

(Formula 2a)

(Formula 2b)
(Formula 2c)
(Formula 2d)
(Formula 2e)
(Formula 2f)

Furthermore, in an embodiment of the present invention, provided is a non-aqueous electrolyte solution for a lithium secondary battery including:

a lithium salt; an organic solvent; and at least one compound of the compounds represented by Formulae 1 and 2.

The compound selected from the group consisting of compounds represented by Formulae 1 and 2 may be included in an amount of about 0.01 wt % to about 10 wt %, for example, 0.5 wt % to 10 wt % based on a total weight of the non-aqueous electrolyte solution. If the amount of the compound is less than 0.01 wt %, an effect of stabilizing a solid electrolyte interface (SEI) film is insignificant, and, in a case in which the amount of the compound is greater than 10 wt %, an increase in resistance due to the surplus additive may occur.

Typically, in a lithium secondary battery, a kind of passivation layer is formed at a position where surface bonding exists at a positive electrode of the battery or at an activated position during charge and discharge by an electrochemical oxidation decomposition reaction of an electrolyte solution. The passivation layer increases impedance for the co-intercalation of lithium ions into a positive electrode active material. Also, during repeated charge and discharge cycles, structural collapse of a positive electrode active material, such as $LiCoO_2$, $LiMn_2O_4$, or $LiNiO_2$, or a chemical dissolution reaction by the electrolyte solution occurs so that cobalt (Co), manganese (Mn), nickel (Ni), iron (Fe), and aluminum (Al) ions are eluted from the positive electrode active material. These reactions not only lead to performance degradation of the positive electrode itself, but also cause a phenomenon in which the eluted metal ions are precipitated and electrodeposited on the surface of a negative electrode.

The metal thus electrodeposited on the negative electrode generally shows large reactivity to the electrolyte solution. Thus, since the movement of the lithium ions is not smooth, an irreversible reaction according to charging and discharging is increased due to a reduction in the amount of reversible lithium, and, as a result, capacity and charge and discharge efficiency of the battery are reduced.

Therefore, in the present invention, at least one of the compounds represented by Formula 1 or 2, which has a high tendency to form a complex with metal ions such as Co, Mn, Ni, Fe, or Al ions, is provided as an electrolyte solution additive. That is, since the compound represented by Formula 1 or 2, which is provided in the present invention, includes an oxygen atom and a propargyl group containing a triple bond that is easily adsorbed to the metal ions, the compound represented by Formula 1 or 2 may form a stable ion conductive film on the surface of the positive electrode while forming a complex by being combined with the metal ions which are eluted from the positive electrode by the structural collapse of the positive electrode active material or the chemical dissolution reaction by the electrolyte solution during charge and discharge.

Furthermore, the compound represented by Formula 1 or 2 may suppress the electrodeposition of the metal ions on the negative electrode by being adsorbed to the metal ions eluted from the positive electrode even in a state in which the film is not formed. Thus, in a case in which the non-aqueous electrolyte solution including the compound represented by Formula 1 or 2 is included, since lithium is smoothly intercalated into and deintercalated from the negative electrode even at high temperature as described later, a secondary battery having significantly improved overall performance, such as room-temperature and high-temperature life characteristics, may be provided.

Since a ketone-based organic solvent has low chemical stability, the ketone-based organic solvent is rarely used as an electrolyte solvent. Thus, in a case in which the compound represented by Formula 2 contains a ketone group (—CO—A—O—$R_6$), in which an alkylene group is bonded to the α-position of a carbonyl group, instead of an ester group (—CO—O—$R_6$), chemical stability may be reduced. Also, in a case in which one or more ether groups unstable to oxidation are further included at $R_6$ position in the compound represented by Formula 2, stability of the non-aqueous electrolyte solution may be reduced and viscosity may be increased.

Also, in the non-aqueous electrolyte solution according to the embodiment of the present invention, the non-aqueous organic solvent and the lithium salt may include any kinds of organic solvents and lithium salts which may be used in a non-aqueous electrolyte solution during the preparation of a typical lithium secondary battery. In this case, amounts thereof may also be appropriately changed in a normally usable range.

Specifically, any lithium salt typically used in an electrolyte solution may be used as the lithium salt without limitation, and, for example, the lithium salt may include $Li^+$ as a cation, and may include at least one selected from the group consisting of $F^-$, $Cl^-$, $Br^-$, $I^-$, $NO_3^-$, $N(CN)_2^-$, $BF_4^-$, $ClO_4^-$, $AlO_4^-$, $AlCl_4^-$, $PF_6^-$, $SbF_6^-$, $AsF_6^-$, $BF_2C_2O_4^-$, $BC_4O_8^-$, $(CF_3)_2PF_4^-$, $(CF_3)_3PF_3^-$, $(CF_3)_4PF_2^-$, $(CF_3)_5PF^-$, $(CF_3)_6P^-$, $CF_3SO_3^-$, $C_4F_9SO_3^-$, $CF_3CF_2SO_3^-$, $(CF_3SO_2)_2N^-$, $(FSO_2)_2N^-$, $CF_3CF_2(CF_3)_2CO^-$, $(CF_3SO_2)_2CH^-$, $CF_3(CF_2)_7SO_3^-$, $CF_3CO_2^-$, $CH_3CO_2^-$, $SCN^-$, and $(CF_3CF_2SO_2)_2N^-$ as an anion. One or, if necessary, a mixture of two or more thereof may be used as the lithium salt. The lithium salt may be appropriately changed in a normally usable range, but may be included in a concentration of 0.8 M to 2 M in the electrolyte solution in order to obtain an optimum anti-corrosion film-forming effect on the surface of the electrode.

Furthermore, any organic solvent typically used in an electrolyte solution for a lithium secondary battery may be used as the organic solvent included in the non-aqueous electrolyte solution of the present invention without limitation, and, for example, an ether compound, an ester compound, an amide compound, a linear carbonate compound, or a cyclic carbonate compound may be used alone or as a mixture of two or more thereof. Among them, the organic solvent may typically include the cyclic carbonate compound, the linear carbonate compound, or a mixture thereof.

Specific examples of the cyclic carbonate compound may be any one selected from the group consisting of ethylene carbonate (EC), propylene carbonate (PC), 1,2-butylene carbonate, 2,3-butylene carbonate, 1,2-pentylene carbonate, 2,3-pentylene carbonate, vinylene carbonate, and fluoroethylene carbonate (FEC), or a mixture of two or more thereof. Also, specific examples of the linear carbonate compound may be any one selected from the group consisting of dimethyl carbonate (DMC), diethyl carbonate (DEC), dipropyl carbonate, ethylmethyl carbonate (EMC), methylpropyl carbonate, and ethylpropyl carbonate, or a mixture of two or more thereof, but the present invention is not limited thereto.

In particular, since ethylene carbonate and propylene carbonate, as cyclic carbonates among the carbonate-based organic solvents, well dissociate the lithium salt in the electrolyte due to high permittivity as highly viscous organic solvents, the ethylene carbonate and propylene carbonate may be preferably used. Since an electrolyte solution having high electrical conductivity may be prepared when the cyclic carbonate is mixed with low viscosity, low permittivity linear carbonate, such as dimethyl carbonate and diethyl carbonate, in an appropriate ratio, the mixed carbonate compound may be more preferably used.

Also, as the ether compound among the organic solvents, any one selected from the group consisting of dimethyl ether, diethyl ether, dipropyl ether, methylethyl ether, methylpropyl ether, and ethylpropyl ether, or a mixture of two or more thereof may be used, but the present invention is not limited thereto.

As the ester compound among the organic solvents, any one selected from the group consisting of linear esters such as methyl acetate, ethyl acetate, propyl acetate, methyl propionate, ethyl propionate, propyl propionate, and butyl propionate; and cyclic esters such as γ-butyrolactone, γ-valerolactone, γ-caprolactone, σ-valerolactone, and ε-caprolactone, or a mixture of two or more thereof may be used, but the present invention is not limited thereto.

Also, in an embodiment of the present invention, provided is a lithium secondary battery including a positive electrode, a negative electrode, a separator disposed between the positive electrode and the negative electrode, and the non-aqueous electrolyte solution of the present invention.

Specifically, the lithium secondary battery of the present invention may be prepared by injecting the non-aqueous electrolyte solution of the present invention into an electrode assembly composed of the positive electrode, the negative electrode, and the separator disposed between the positive electrode and the negative electrode. In this case, any positive electrode, negative electrode, and separator, which have typically been used in the preparation of a lithium secondary battery, may be used as the positive electrode, negative electrode, and separator which constitute the electrode assembly.

The positive electrode may be prepared by coating a positive electrode collector with a positive electrode slurry including a positive electrode active material, a binder, a conductive agent, and a solvent, and then drying and rolling the coated positive electrode collector.

The positive electrode collector is not particularly limited so long as it has conductivity without causing adverse chemical changes in the battery, and, for example, stainless steel, aluminum, nickel, titanium, fired carbon, or aluminum or stainless steel that is surface-treated with one of carbon, nickel, titanium, silver, or the like may be used.

The positive electrode active material is a compound capable of reversibly intercalating and deintercalating lithium, wherein the positive electrode active material may specifically include a lithium composite metal oxide including lithium and at least one metal such as cobalt, manganese, nickel, or aluminum. Specifically, the lithium composite metal oxide may include lithium-manganese-based oxide (e.g., $LiMnO_2$, $LiMn_2O_4$, etc.), lithium-cobalt-based oxide (e.g., $LiCoO_2$, etc.), lithium-nickel-based oxide (e.g., $LiNiO_2$, etc.), lithium-nickel-manganese-based oxide (e.g., $LiNi_{1-Y}Mn_YO_2$ (where $0<Y<1$), $LiMn_{2-Z}Ni_ZO_4$ (where $0<Z<2$), etc.), lithium-nickel-cobalt-based oxide (e.g., $LiNi_{1-Y1}Co_{Y1}O_2$ (where $0<Y1<1$), lithium-manganese-cobalt-based oxide (e.g., $LiCo_{1-Y2}Mn_{Y2}O_2$ (where $0<Y2<1$), $LiMn_{2-Z1}Co_{Z1}O_4$ (where $0<Z1<2$), etc.), lithium-nickel-manganese-cobalt-based oxide (e.g., $Li(Ni_pCo_qMn_{r1})O_2$ (where $0<p<1$, $0<q<1$, $0<r1<1$, and $p+q+r1=1$) or $Li(Ni_{p1}Co_{q1}Mn_{r2})O_4$ (where $0<p1<2$, $0<q1<2$, $0<r2<2$, and $p1+q1+r2=2$), etc.), or lithium-nickel-cobalt-transition metal (M) oxide (e.g., $Li(Ni_{p2}Co_{q2}Mn_{r3}M_{s2})O_2$ (where M is selected from the group consisting of aluminum (Al), iron (Fe), vanadium (V), chromium (Cr), titanium (Ti), tantalum (Ta), magnesium (Mg), and molybdenum (Mo), and p2, q2, r3, and s2 are atomic fractions of each independent elements, wherein $0<p2<1$, $0<q2<1$, $0<r3<1$, $0<S2<1$, and $p2+q2+r3+S2=1$), etc.), and any one thereof or a compound of two or more thereof may be included. Among these materials, in terms of the improvement of capacity characteristics and stability of the battery, the lithium composite metal oxide may include $LiCoO_2$, $LiMnO_2$, $LiNiO_2$, lithium nickel manganese cobalt oxide (e.g., $Li(Ni_{0.6}Mn_{0.2}Co_{0.2})O_2$, $Li(Ni_{0.5}Mn_{0.3}Co_{0.2})O_2$, or $Li(Ni_{0.8}Mn_{0.1}Co_{0.1})O_2$), or lithium nickel cobalt aluminum oxide (e.g., $LiNi_{0.8}Co_{0.15}Al_{0.05}O_2$, etc.), and, in consideration of a significant improvement due to the control of type and content ratio of elements constituting the lithium composite metal oxide, the lithium composite metal oxide may include $Li(Ni_{0.6}Mn_{0.2}CO_{0.2})O_2$, $Li(Ni_{0.5}Mn_{0.3}Co_{0.2})O_2$, $Li(Ni_{0.7}Mn_{0.15}Co_{0.15})O_2$, or $Li(Ni_{0.8}Mn_{0.1}Co_{0.1})O_2$, and any one thereof or a mixture of two or more thereof may be used.

The positive electrode active material may be included in an amount of 80 wt % to 99 wt % based on a total weight of solid content in the positive electrode slurry.

Also, the binder is a component that assists in the binding between the active material and the conductive agent and in the binding with the current collector, wherein the binder is commonly added in an amount of 1 wt % to 30 wt % based on the total weight of the solid content in the positive electrode slurry. Examples of the binder may be polyvinylidene fluoride, polyvinyl alcohol, carboxymethylcellulose (CMC), starch, hydroxypropylcellulose, regenerated cellulose, polyvinylpyrrolidone, tetrafluoroethylene, polyethylene, polypropylene, an ethylene-propylene-diene terpolymer (EPDM), a sulfonated EPDM, a styrene-butadiene rubber, a fluoro rubber, various copolymers, and the like.

Furthermore, the conductive agent is a material providing conductivity while not causing chemical changes in the battery, wherein the conductive agent may be added in an amount of 1 wt % to 20 wt % based on the total weight of the solid content in the positive electrode slurry.

As typical examples of the conductive agent, a conductive material, such as: carbon powder such as carbon black, acetylene black, Ketjen black, channel black, furnace black, lamp black, or thermal black; graphite powder such as natural graphite with a well-developed crystal structure, artificial graphite, or graphite; conductive fibers such as carbon fibers or metal fibers; metal powder such as fluorocarbon powder, aluminum powder, and nickel powder; conductive whiskers such as zinc oxide whiskers and potassium titanate whiskers; conductive metal oxide such as titanium oxide; or polyphenylene derivatives, may be used, and those currently sold under the names, such as acetylene black-based conductive agents (Chevron Chemical Company, Denka black (Denka Singapore Private Limited), or Gulf Oil Company), Ketjen black, ethylene carbonate (EC)-based conductive agents (Armak Company), Vulcan XC-72 (Cabot Company), and Super P (Timcal Graphite & Carbon), may be used.

Also, the solvent may include an organic solvent, such as N-methyl-2-pyrrolidone (NMP), and may be used in an amount such that desirable viscosity is obtained when the positive electrode active material as well as selectively the binder and the conductive agent are included. For example, the solvent may be included in an amount such that a concentration of the solid content in the slurry including the positive electrode active material as well as selectively the binder and the conductive agent is in a range of 10 wt % to 60 wt %, for example, 20 wt % to 50 wt %.

Furthermore, the negative electrode, for example, may be prepared by coating a negative electrode collector with a negative electrode slurry including a negative electrode active material, a binder, a conductive agent, and a solvent, and then drying and rolling the coated negative electrode collector.

The negative electrode collector generally has a thickness of 3 μm to 500 μm. The negative electrode collector is not particularly limited so long as it has high conductivity without causing adverse chemical changes in the battery, and, for example, copper, stainless steel, aluminum, nickel, titanium, fired carbon, copper or stainless steel that is surface-treated with one of carbon, nickel, titanium, silver, or the like, an aluminum-cadmium alloy, or the like may be used. Also, similar to the positive electrode collector, the negative electrode collector may have fine surface roughness to improve bonding strength with the negative electrode active material, and the negative electrode collector may be used in various shapes such as a film, a sheet, a foil, a net, a porous body, a foam body, a non-woven fabric body, and the like.

The negative electrode active material may include at least one selected from the group consisting of lithium metal, a carbon material capable of reversibly intercalating/deintercalating lithium ions, metal or an alloy of lithium and the metal, a metal composite oxide, a material which may be doped and undoped with lithium, and a transition metal oxide.

As the carbon material capable of reversibly intercalating/deintercalating lithium ions, a carbon-based negative electrode active material generally used in a lithium ion secondary battery may be used without particular limitation, and, as a typical example, crystalline carbon, amorphous carbon, or both thereof may be used. Examples of the crystalline carbon may be graphite such as irregular, planar, flaky, spherical, or fibrous natural graphite or artificial graphite, and examples of the amorphous carbon may be soft carbon (low-temperature sintered carbon) or hard carbon, mesophase pitch carbide, and fired cokes.

As the metal or the alloy of lithium and the metal, a metal selected from the group consisting of copper (Cu), nickel (Ni), sodium (Na), potassium (K), rubidium (Rb), cesium (Cs), francium (Fr), beryllium (Be), magnesium (Mg), calcium (Ca), strontium (Sr), silicon (Si), antimony (Sb), lead (Pb), indium (In), zinc (Zn), barium (Ba), radium (Ra), germanium (Ge), aluminum (Al), and tin (Sn), or an alloy of lithium and the metal may be used.

One selected from the group consisting of PbO, $PbO_2$, $Pb_2O_3$, $Pb_3O_4$, $Sb_2O_3$, $Sb_2O_4$, $Sb_2O_5$, GeO, $GeO_2$, $Bi_2O_3$, $Bi_2O_4$, $Bi_2O_5$, $Li_xFe_2O_3$ ($0 \le x \le 1$), $Li_xWO_2$ ($0 < x \le 1$), and $Sn_xMe_{1-x}Me'_yO_x$ (Me: manganese (Mn), Fe, Pb, or Ge; Me': Al, boron (B), phosphorus (P), Si, Groups I, II and III elements of the periodic table, or halogen; $0 < x \le 1$; $1 \le y \le 3$; $1 \le z \le 8$) may be used as the metal composite oxide.

The material, which may be doped and undoped with lithium, may include Si, $SiO_x$ ($0 < x < 2$), a Si—Y alloy (where Y is an element selected from the group consisting of alkali metal, alkaline earth metal, a Group 13 element, a Group 14 element, transition metal, a rare earth element, and a combination thereof, and is not Si), Sn, $SnO_2$, and Sn—Y (where Y is an element selected from the group consisting of alkali metal, alkaline earth metal, a Group 13 element, a Group 14 element, transition metal, a rare earth element, and a combination thereof, and is not Sn), and a mixture of $SiO_2$ and at least one thereof may also be used. The element Y may be selected from the group consisting of Mg, Ca, Sr, Ba, Ra, scandium (Sc), yttrium (Y), Ti, zirconium (Zr), hafnium (Hf), rutherfordium (Rf), V, niobium (Nb), Ta, dubidium (Db), Cr, Mo, tungsten (W), seaborgium (Sg), technetium (Tc), rhenium (Re), bohrium (Bh), Fe, Pb, ruthenium (Ru), osmium (Os), hassium (Hs), rhodium (Rh), iridium (Ir), palladium (Pd), platinum (Pt), Cu, silver (Ag), gold (Au), Zn, cadmium (Cd), B, Al, gallium (Ga), Sn, In, Ge, P, arsenic (As), Sb, bismuth (Bi), sulfur (S), selenium (Se), tellurium (Te), polonium (Po), and a combination thereof.

The transition metal oxide may include lithium-containing titanium composite oxide (LTO), vanadium oxide, and lithium vanadium oxide.

The negative electrode active material may be included in an amount of 80 wt % to 99 wt % based on a total weight of solid content in the negative electrode slurry.

Also, the binder is a component that assists in the binding between the conductive agent, the active material, and the current collector, wherein the binder is commonly added in an amount of 1 wt % to 30 wt % based on the total weight of the solid content in the negative electrode slurry. Examples of the binder may be polyvinylidene fluoride, polyvinyl alcohol, carboxymethylcellulose (CMC), starch, hydroxypropylcellulose, regenerated cellulose, polyvinylpyrrolidone, tetrafluoroethylene, polyethylene, polypropylene, an ethylene-propylene-diene polymer (EPDM), a sulfonated EPDM, a styrene-butadiene rubber, a fluoro rubber, and various copolymers thereof.

Furthermore, the conductive agent is a component for further improving the conductivity of the negative electrode active material, wherein the conductive agent may be added in an amount of 1 wt % to 20 wt % based on the total weight of the solid content in the negative electrode slurry. Any conductive agent may be used without particular limitation so long as it has conductivity without causing adverse chemical changes in the battery, and, for example, a conductive material such as: graphite such as natural graphite or artificial graphite; carbon black such as acetylene black, Ketjen black, channel black, furnace black, lamp black, and thermal black; conductive fibers such as carbon fibers and metal fibers; metal powder such as fluorocarbon powder, aluminum powder, and nickel powder; conductive whiskers such as zinc oxide whiskers and potassium titanate whiskers; conductive metal oxide such as titanium oxide; or polyphenylene derivatives may be used.

The solvent may include water or an organic solvent, such as NMP and alcohol, and may be used in an amount such that desirable viscosity is obtained when the negative electrode active material as well as selectively the binder and the conductive agent are included. For example, the solvent may be included in an amount such that a concentration of the solid content including the negative electrode active material as well as selectively the binder and the conductive agent is in a range of 50 wt % to 75 wt %, for example, 50 wt % to 65 wt %.

Also, a typical porous polymer film used as a typical separator, for example, a porous polymer film prepared from a polyolefin-based polymer, such as an ethylene homopolymer, a propylene homopolymer, an ethylene-butene copolymer, an ethylene-hexene copolymer, and an ethylene-methacrylate copolymer, may be used alone or in a lamination therewith as the separator. Also, a typical porous nonwoven fabric, for example, a nonwoven fabric formed of high melting point glass fibers or polyethylene terephthalate fibers may be used, but the present invention is not limited thereto.

A shape of the lithium secondary battery of the present invention is not particularly limited, but a cylindrical type using a can, a prismatic type, a pouch type, or a coin type may be used.

Hereinafter, the present invention will be described in more detail according to examples. However, the invention may be embodied in many different forms and should not be construed as being limited to the embodiments set forth herein. Rather, these example embodiments are provided so that this description will be thorough and complete, and will fully convey the scope of the present invention to those skilled in the art.

EXAMPLES

Example 1

(Non-aqueous Electrolyte Solution Preparation)

A non-aqueous electrolyte solution of the present invention was prepared by adding 0.5 g of the compound represented by Formula 1a to 99.5 g of a non-aqueous organic solvent (ethylene carbonate (EC):ethyl methyl carbonate (EMC)=volume ratio of 30:70) in which 1 M $LiPF_6$ was dissolved.

(Secondary Battery Preparation)

40 parts by weight of a mixture, in which lithium cobalt composite oxide ($LiCO_2$) as positive electrode active material particles, carbon black as a conductive agent, and polyvinylidene fluoride, as a binder, were mixed in a weight ratio of 90:5:5, was added to 100 parts by weight of N-methyl-2-pyrrolidone (NMP), as a solvent, to prepare a positive electrode active material slurry composition. A 100 μm thick positive electrode collector (Al thin film) was coated with the positive electrode active material slurry composition, dried, and roll-pressed to prepare a positive electrode.

80 parts by weight of a mixture, in which natural graphite as a negative electrode active material, polyvinylidene fluoride as a binder, and carbon black, as a conductive agent, were mixed in a weight ratio of 95:2:3, was added to 100 parts by weight of NMP, as a solvent, to prepare a negative electrode active material slurry composition. A 90 μm thick negative electrode collector (Cu thin film) was coated with the negative electrode active material slurry composition, dried, and roll-pressed to prepare a negative electrode.

An electrode assembly was prepared by stacking the positive electrode prepared by the above-described method, a polyethylene porous film and negative electrode prepared by the above-described method, and a lithium secondary battery was then prepared by putting the electrode assembly in a battery case, injecting the prepared non-aqueous electrolyte solution thereinto, and sealing the battery case.

Example 2

A non-aqueous electrolyte solution and a secondary battery including the same were prepared in the same manner as in Example 1 except that the compound of Formula 1b, instead of the compound of Formula 1a, was included during the preparation of the non-aqueous electrolyte solution.

Example 3

A non-aqueous electrolyte solution and a secondary battery including the same were prepared in the same manner as in Example 1 except that the compound of Formula 1c, instead of the compound of Formula 1a, was included during the preparation of the non-aqueous electrolyte solution.

Example 4

A non-aqueous electrolyte solution and a secondary battery including the same were prepared in the same manner as in Example 1 except that the compound of Formula 1d, instead of the compound of Formula 1a, was included as an additive during the preparation of the non-aqueous electrolyte solution.

Example 5

A non-aqueous electrolyte solution and a secondary battery including the same were prepared in the same manner as in Example 1 except that the compound of Formula 1e, instead of the compound of Formula 1a, was included during the preparation of the non-aqueous electrolyte solution.

Example 6

A non-aqueous electrolyte solution and a secondary battery including the same were prepared in the same manner as in Example 1 except that the compound of Formula 1f, instead of the compound of Formula 1a, was included during the preparation of the non-aqueous electrolyte solution.

Example 7

A non-aqueous electrolyte solution and a secondary battery including the same were prepared in the same manner as in Example 1 except that the compound of Formula 1g, instead of the compound of Formula 1a, was included during the preparation of the non-aqueous electrolyte solution.

Example 8

A non-aqueous electrolyte solution and a secondary battery including the same were prepared in the same manner as in Example 1 except that the compound of Formula 2a, instead of the compound of Formula 1a, was included during the preparation of the non-aqueous electrolyte solution.

Example 9

A non-aqueous electrolyte solution and a secondary battery including the same were prepared in the same manner as in Example 1 except that the compound of Formula 2b, instead of the compound of Formula 1a, was included during the preparation of the non-aqueous electrolyte solution.

Example 10

A non-aqueous electrolyte solution and a secondary battery including the same were prepared in the same manner as in Example 1 except that the compound of Formula 2c, instead of the compound of Formula 1a, was included during the preparation of the non-aqueous electrolyte solution.

Example 11

A non-aqueous electrolyte solution and a secondary battery including the same were prepared in the same manner as in Example 1 except that the compound of Formula 2d, instead of the compound of Formula 1a, was included during the preparation of the non-aqueous electrolyte solution.

Example 12

A non-aqueous electrolyte solution and a secondary battery including the same were prepared in the same manner as in Example 1 except that the compound of Formula 2e, instead of the compound of Formula 1a, was included during the preparation of the non-aqueous electrolyte solution.

Example 13

A non-aqueous electrolyte solution and a secondary battery including the same were prepared in the same manner as in Example 1 except that the compound of Formula 2f, instead of the compound of Formula 1a, was included during the preparation of the non-aqueous electrolyte solution.

Example 14

A non-aqueous electrolyte solution and a secondary battery including the same were prepared in the same manner as in Example 1 except that 10 g of the compound of Formula 1a was included as an additive in 90 g of a non-aqueous organic solvent during the preparation of the non-aqueous electrolyte solution.

Example 15

A non-aqueous electrolyte solution and a secondary battery including the same were prepared in the same manner as in Example 1 except that 15 g of the compound of Formula 1a was added to 85 g of a non-aqueous organic solvent during the preparation of the non-aqueous electrolyte solution.

Comparative Example 1

A non-aqueous electrolyte solution and a secondary battery including the same were prepared in the same manner as in Example 1 except that an additive was not included during the preparation of the non-aqueous electrolyte solution.

EXPERIMENTAL EXAMPLES

Experimental Example 1

Figure 1:
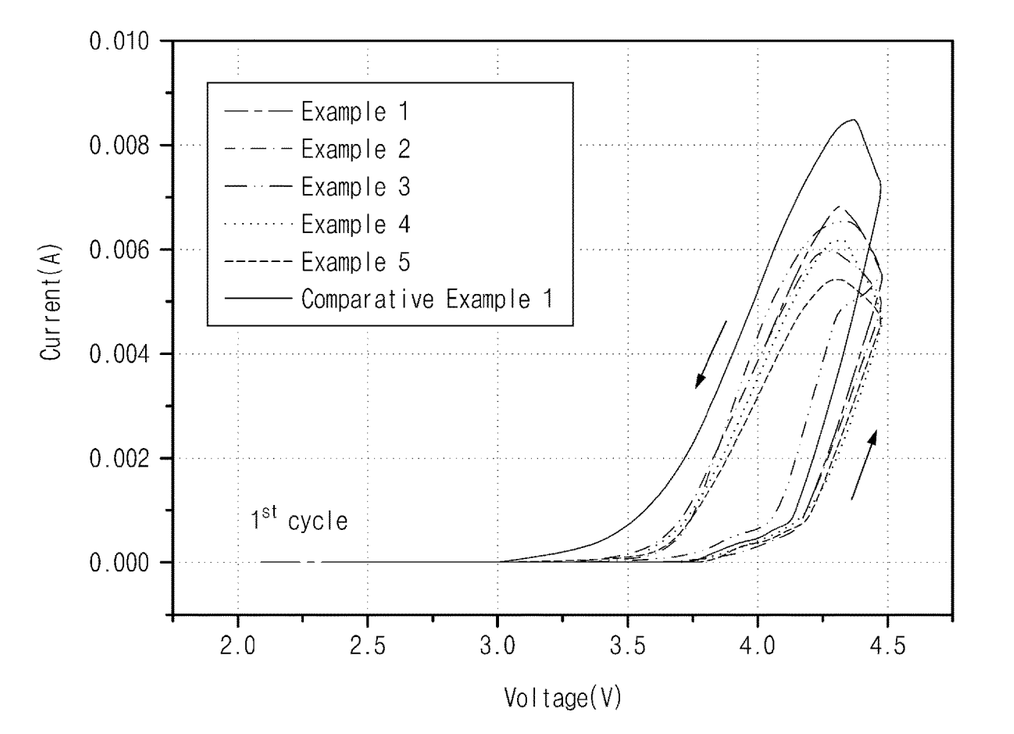
The Figure is a graph illustrating the results of cyclic voltammetry of a non-aqueous electrolyte solution according to Experimental Example 1 of the present invention.

The non-aqueous electrolyte solutions prepared in Examples 1 to 5 and Comparative Example 1 were respectively investigated by cyclic voltammetry while using a Fe foil, as a working electrode, and lithium metal as a counter electrode and a reference electrode. A potentiostat/galvanostat (Model 273A, EG & G Princeton Applied Research) was used as a measuring instrument. In this case, measurements were made within a voltage range of 2.5 V to 4.5 V (vs. Li/Li$^+$) from open circuit voltage (OCV) at a voltage scan rate of 5 mV/sec. The measurement results are illustrated in the Figure below.

As illustrated in the Figure, since Comparative Example 1 using the non-aqueous electrolyte solution without the additive showed a high current peak in the first cycle, it was considered that a large amount of Fe dissolution occurred. In contrast, it may be understood that the non-aqueous electrolyte solutions prepared in Examples 1 to 5, which respectively included the compounds of Formulae 1a to 1e including a triple bond, showed lower current peaks than Comparative Example 1 in the first cycle. That is, from these results, it may be understood that the compounds of Formulae 1a to 1e including a triple bond suppressed the Fe dissolution by forming a film on the surface of the Fe foil as the working electrode.

Experimental Example 2

Fe particles having a diameter of 280 μm to 330 μm were disposed between the positive electrode and the separator during the preparation of the secondary batteries in Examples 1 to 15 and Comparative Example 1. Eight samples for each of the secondary batteries of Examples 1 to 15 and Comparative Example 1 were prepared in this manner. Each secondary battery (battery capacity 5.5 mAh) thus prepared was charged at a constant current of 0.1 C to a voltage of 4.2 V at 25° C. Thereafter, each battery was charged at a constant voltage of 4.2 V and the charge was terminated when a charge current became 0.275 mA. After each battery was left standing for 10 minutes, each battery was discharged at a constant current of 0.5 C to a voltage of 3.0 V. The number of chargeable and dischargeable secondary batteries among the eight secondary batteries for each Example and Comparative Example was checked and listed in the following Table 1.

Subsequently, the chargeable and dischargeable secondary batteries were charged at a 0.8 C rate to 4.2 V under a constant current/constant voltage condition and stored at 45° C. for 6 days. After 6 days of storage, voltages were measured at 45° C. and listed in the following Table 1.

TABLE 1

| | Additive | | Residual | Recovery | Cycle |
|---|---|---|---|---|---|
| | Formula | Amount (%) | discharge capacity (%) | discharge capacity (%) | capacity retention (%) |
| Example 1 | 1a | 0.5 | 83 | 96 | 88 |
| Example 2 | 1b | 0.5 | 83 | 95 | 86 |
| Example 3 | 1c | 0.5 | 85 | 93 | 85 |
| Example 4 | 1d | 0.5 | 85 | 95 | 88 |
| Example 5 | 1e | 0.5 | 80 | 95 | 85 |
| Example 6 | 1f | 0.5 | 80 | 93 | 90 |
| Example 7 | 1g | 0.5 | 85 | 93 | 87 |
| Example 8 | 2a | 0.5 | 81 | 96 | 90 |
| Example 9 | 2b | 0.5 | 84 | 96 | 90 |
| Example 10 | 2c | 0.5 | 80 | 94 | 88 |
| Example 11 | 2d | 0.5 | 83 | 92 | 90 |
| Example 12 | 2e | 0.5 | 85 | 94 | 87 |
| Example 13 | 2f | 0.5 | 82 | 93 | 90 |
| Example 14 | 1a | 10 | 83 | 93 | 82 |
| Example 15 | 1a | 15 | 80 | 85 | 45 |

TABLE 1-continued

| Additive | | Residual discharge capacity (%) | Recovery discharge capacity (%) | Cycle capacity retention (%) |
|---|---|---|---|---|
| Formula | Amount (%) | | | |
| Comparative Example 1 | — | — | 64 | 75 | 57 |

As illustrated in Table 1, with respect to the secondary batteries prepared in Examples 1 to 15 which respectively included the non-aqueous electrolyte solutions of the present invention, it may be understood that residual discharge capacities, recovery discharge capacities, and cycle capacities were maintained even if the cycles proceeded at high temperature, but the secondary battery of Comparative Example 1 including the non-aqueous electrolyte solution without a non-aqueous electrolyte solution additive had low residual capacity, recovery discharge capacity, and cycle capacity retention.

In this case, with respect to the secondary battery of Example 15 which included the non-aqueous electrolyte solution including an excessive amount of the non-aqueous electrolyte solution additive, it may be understood that the residual capacity and recovery discharge capacity were maintained at the same level as those of the secondary batteries of Examples 1 to 14, but the cycle capacity retention was reduced in comparison to that of the secondary battery of Comparative Example 1 without the non-aqueous electrolyte solution additive due to an increase in resistance caused by the surplus additive.

The invention claimed is:

1. A non-aqueous electrolyte solution for a lithium secondary battery, the non-aqueous electrolyte solution comprising:
a lithium salt;
an organic solvent; and
an additive for a non-aqueous electrolyte solution, wherein the additive comprises at least one compound represented by Formulae 1 or 2:

(Formula 1)

(Formula 2)

wherein, in Formula 1 or 2,
$R_1$ and $R_2$ are each independently hydrogen, an alkyl group having 1 to 6 carbon atoms, or alkoxy having 1 to 6 carbon atoms,
$R_3$ is an alkylene group having 1 to 3 carbon atoms,
$R_4$ is hydrogen, an alkyl group having 1 to 6 carbon atoms, an aryl group having 6 to 18 carbon atoms, a heterocycloalkyl group having 5 to 8 carbon atoms, an alkenyl group having 2 to 4 carbon atoms, or an alkynyl group having 2 to 4 carbon atoms, wherein the alkyl group, the aryl group, the heterocycloalkyl group, the alkenyl group and the alkynyl group are not further substituted,
$R_5$ is an alkyl group having 2 to 4 carbon atoms which includes an ether group,
$R_6$ is hydrogen, an alkyl group having 1 to 6 carbon atoms, an aryl group having 6 to 18 carbon atoms, a heterocycloalkyl group having 5 to 8 carbon atoms, an alkenyl group having 2 to 4 carbon atoms, or an alkynyl group having 2 to 4 carbon atoms, and
n is an integer of 0 to 3,
wherein when $R_4$ is H or an aryl group having 6 carbon atoms, and n is 0, $R_1$ is not hydrogen, and
wherein when $R_6$ is an alkyl group having 1 to 6 carbon atoms, the alkyl group is not further substituted; and when $R_6$ is an aryl group having 6 to 18 carbon atoms, the aryl group is a phenyl group, a halophenyl group, a tolyl group, a naphthyl group, a trihalophenyl group, a trihalomethylphenyl group, an anthryl group, or a phenanthryl group, each of which is not further substituted.

2. The non-aqueous electrolyte solution for a lithium secondary battery of claim 1, wherein in Formula 1,
$R_1$ is hydrogen or an alkyl group having 1 to 6 carbon atoms,
$R_2$ is hydrogen or alkoxy having 1 to 6 carbon atoms,
$R_3$ is an alkylene group having 1 to 3 carbon atoms,
$R_4$ is an alkyl group having 1 to 6 carbon atoms, an aryl group having 6 to 18 carbon atoms, a heterocycloalkyl group having 5 to 8 carbon atoms, or an alkynyl group having 2 to 4 carbon atoms, each of which is not further substituted, and
n is an integer of 0 to 3.

3. The non-aqueous electrolyte solution for a lithium secondary battery of claim 1, wherein in Formula 2,
$R_5$ is an alkyl group having 2 to 4 carbon atoms which includes an ether group, and $R_6$ is an alkyl group having 1 to 6 carbon atoms.

4. The non-aqueous electrolyte solution for a lithium secondary battery of claim 1, wherein the additive for a non-aqueous electrolyte solution is included in an amount of 0.01 wt% to 10 wt% based on a total weight of the non-aqueous electrolyte solution.

5. The non-aqueous electrolyte solution for a lithium secondary battery of claim 4, wherein the additive for a non-aqueous electrolyte solution is included in an amount of 0.5 wt% to 10 wt% based on the total weight of the non-aqueous electrolyte solution.

6. A lithium secondary battery comprising a negative electrode, a positive electrode, and a non-aqueous electrolyte solution,
wherein the non-aqueous electrolyte solution comprises the non-aqueous electrolyte solution for a lithium secondary battery of claim 1.

7. A non-aqueous electrolyte solution for a lithium secondary battery, the non-aqueous electrolyte solution comprising:
a lithium salt;
an organic solvent; and
an additive for a non-aqueous electrolyte solution, wherein the additive comprises at least one compound represented by Formulae 1a to 1f:

(Formula 1a)

(Formula 1b)

(Formula 1c)

-continued (Formula 1d)

(Formula 1e)

(Formula 1f)

8. A non-aqueous electrolyte solution for a lithium secondary battery, the non-aqueous electrolyte solution comprising:
a lithium salt;
an organic solvent; and
an additive for a non-aqueous electrolyte solution, wherein the additive comprises at least one compound represented by Formulae 2e or 2f:

(Formula 2e)

(Formula 2f)

* * * * *